United States Patent [19]

Chelu

[11] Patent Number: 4,550,010
[45] Date of Patent: Oct. 29, 1985

[54] PROCESS FOR DEODORIZING POLLUTED AIR

[75] Inventor: Gérard Chelu, Verneuil en Halatte, France

[73] Assignee: Charbonnages de France, Paris, France

[21] Appl. No.: 339,737

[22] Filed: Jan. 15, 1982

[30] Foreign Application Priority Data

Jan. 19, 1981 [FR] France ................. 81 00906

[51] Int. Cl.[4] .................. A61L 9/015; A61L 9/14
[52] U.S. Cl. ............................. 422/4; 422/3; 422/5; 422/62; 422/120; 422/122; 423/224
[58] Field of Search ............. 422/3, 4, 111, 120, 422/122, 62, 5; 423/210 R, 224

[56] References Cited

U.S. PATENT DOCUMENTS

| 1,423,704 | 7/1922 | Wolff | 422/4 |
|---|---|---|---|
| 3,969,479 | 7/1976 | Lonnes et al. | 423/210 |
| 4,172,880 | 10/1979 | Tzavos | 422/4 X |
| 4,208,383 | 6/1980 | Kisters et al. | 423/210 R X |
| 4,307,067 | 12/1981 | Tagawa et al. | 422/5 X |
| 4,460,552 | 7/1984 | Zakrzewski | 422/3 X |

FOREIGN PATENT DOCUMENTS

| 706750 | 6/1931 | France . |
|---|---|---|
| 2150966 | 4/1973 | France . |
| 2187729 | 1/1974 | France . |
| 2229447 | 12/1974 | France . |
| 2271862 | 12/1975 | France . |
| 2281908 | 4/1979 | France . |
| 2416016 | 8/1980 | France . |
| 49-123173 | 11/1974 | Japan ................. 423/224 |
| 54-101764 | 8/1979 | Japan ................. 423/224 |
| 55-094623 | 7/1980 | Japan ................. 423/224 |

OTHER PUBLICATIONS

Chemical Abstracts, vol. 92, 1980, p. 302, Ref 92:46756d.
Japanese Patent Gazette, Part I, Chemical Week X24-Unexamined, Ref 44446x/24.

Primary Examiner—Barry S. Richman
Assistant Examiner—Brion P. Heaney
Attorney, Agent, or Firm—Cushman, Darby & Cushman

[57] ABSTRACT

A process for deodorizing polluted air, wherein the air to be deodorized is washed in a washing apparatus with an aqueous solution of hydrogen peroxide. The solution is circulated in a closed circuit while ozone is introduced either directly into the air to be treated or directly into the aqueous solution which is thus regenerated. The initial weight percentage of hydrogen peroxide in the aqueous solution is within the range of 0.5% to 10%.

9 Claims, 1 Drawing Figure

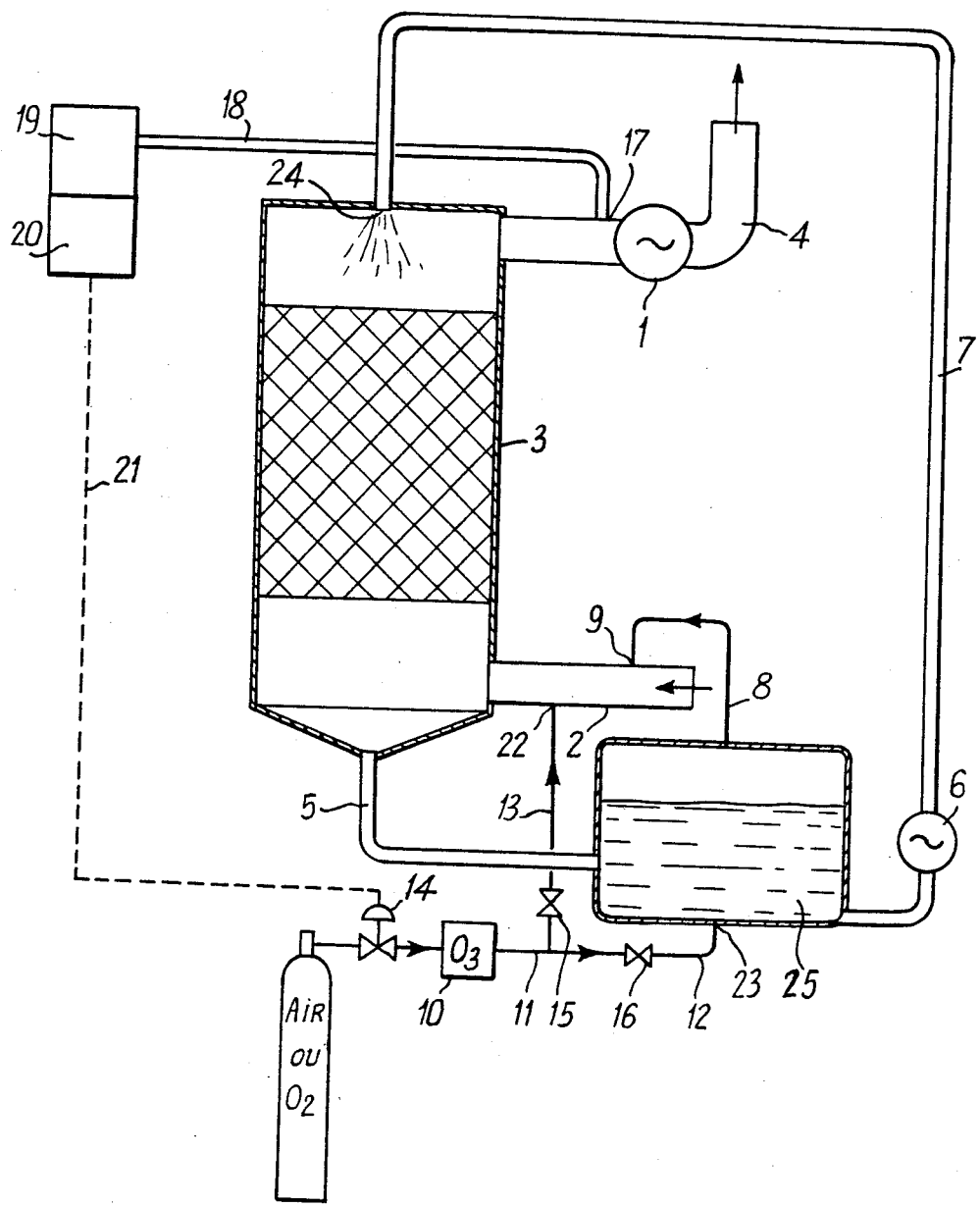

PROCESS FOR DEODORIZING POLLUTED AIR

BACKGROUND OF THE INVENTION

The invention relates to a process for deodorizing polluted air containing ill-smelling gaseous residues or organic origin, in which the air to be deodorized is treated with ozone and washed in a washing apparatus by means of an aqueous solution.

In numerous factories, such as for example knackers' yards, tallow-melting houses, waste-water treating plants, the presence of ill-smelling compounds in the gaseous effluents is an important cause of environmental problems. To remove these odours, numerous processes have already been proposed, such as oxidizing washing with multiple variants, adsorption over activated carbon, thermal oxidation at high temperature or catalytic oxidation at more moderate temperature, oxidation by ozone at ambient temperature possibly completed by a washing as in the process mentioned above. Most of these processes are not sufficiently efficient or are of prohibitive cost.

The main compounds responsible for nauseous odours are sulfurated compounds, particularly hydrogen sulfide, and mercaptans such as methyl mercaptan, ammonia and amines, such as trimethylamine, aldehydes such as acrolein, valeraldehyde, butyraldehyde, ketones, such as methyléthylketone. Although most of the sulfurated and ammoniated compounds react with ozone, this does not apply to aldehydes.

It is an object of the invention to propose a process for neutralizing, in one treatment and at ambient temperature, the ill-smelling compounds, and more particularly those of the above-mentioned families, whether or not they are identified by analysis. It is a further object of the invention to propose a process which is highly efficient, easy to carry out, and consuming little oxidizing agent due to adjustment thereof as a function of needs.

SUMMARY OF THE INVENTION

By carrying out a process of the type described hereinabove and by using an aqueous solution of hydrogen peroxide in the initial ratio of 0.5/100 to 10/100 by mass of the solution, and preferably of the order of 5/100, Applicant has observed that the deodorization of the polluted air is complete with neutralisation, even at ambient temperature, of all the above-mentioned compounds. However, Applicant has further unexpectedly observed that, if the aqueous solution of hydrogen peroxide is recycled, injection of ozone suffices to maintain the strength of this hydrogen peroxide at its initial value; in that case, it is no longer necessary to provide an addition of hydrogen peroxide, the simple addition of ozone being sufficient. Without there being a scientifically established explanation, it is possible that the process according to the invention promotes the radical formation of peroxides in the aqueous solution. As the case may be, by introducing hydrogen peroxide in the initial liquid phase only, there is no need to introduce any subsequently, this rendering the process very economical, whilst neutralising the compounds such as aldehydes, which the ozone + washing water treatment does not neutralise.

The addition of hydrogen peroxide according to the invention differs from preceding uses of this compound which is usually introduced into the liquid or solid phase of the waste, products or other refuse as in French Pat. Nos. 2 187 729, 2 281 908 or 2 416 016 where hydrogen peroxide up to about 500 ppm is used and/or consumed. In the invention, apart from the initial addition, no added hydrogen peroxide is consumed.

It is therefore important according to the invention that the aqueous washing solution is circulated in a closed circuit.

According to one embodiment, ozone is introduced into the polluted air before it is washed with the aqueous solution, as is known per se.

However, according to a preferred embodiment of the invention, the ozone is introduced into the washing circuit, for example by bubbling in the aqueous washing solution dwelling in a buffer tank.

According to an economical embodiment of the invention, the gaseous phase not absorbed following introduction of the ozone in the aqueous washing solution in the buffer tank is recovered and said recovered gaseous phase is introduced into the polluted air before it is washed with the aqueous solution.

According to an interesting feature of the invention, the rate of flow of ozone introduced is adjusted as a function of a reference value of the quantity of ozone metered in the effluent air leaving the washing apparatus.

In this way, a quasi-stoichiometric adjustment of the quantity of ozone introduced and therefore consumed is obtained, which allows the process to be carried out particularly economically.

BRIEF DESCRIPTION OF THE DRAWINGS

The invention will be more readily understood on reading the following description with reference to the accompanying drawings, in which:

The single FIGURE is a diagram, not to a defined scale, of an installation according to the invention for washing polluted air or gaseous effluents coming from a treatment vat or a dwelling tank for nauseous organic products or waste.

DESCRIPTION OF THE PREFERRED EMBODIMENTS

Referring now to the drawing, polluted air to be treated is evacuated to the atmosphere by an exhauster 1 through a pipe 4, a washing apparatus 3 incorporating a surface washer and another pipe 2. At the top of the washing apparatus 3, an aqueous solution coming from an air-tight tank 25 is conducted by a pump 6 through a pipe 7 and nozzles 24. A pipe 5 emerges from the base of the washing apparatus which recycles the aqueous solution to tank 25. A source of ozone 10 sends ozone to one of two pipes 12 or 13, as desired, by means of a valve 15 and valve 16, respectively. Pipe 13 enables the ozone to be conducted to an inlet point 22 in pipe 2, i.e. into the polluted air to be treated. Pipe 12 enables the ozone to be conducted to an inlet point 23 at the bottom of the tank 25 and bubbled into the aqueous solution. A pipe 8 emerges at the top of the tank 25, said pipe leading to an inlet point 9 in the pipe 2, i.e. also into the polluted air to be treated. It will be seen that, in the first case, the ozone is introduced into the aqueous phase where it will act actively, but that the ozone not consumed will encounter the aqueous solution in the washing apparatus 3 in counter-current and be absorbed in the liquid phase. In the second case, the ozone firstly enriches the liquid phase by absorption by bubbling, then acts directly on the gaseous phase to be purified.

According to a simple mode of adjustment, the quantity of ozone introduced may be associated with the quantity of reduced sulfurated products contained in the gases. An equimolecular quantity of ozone is sufficient. However, according to a preferred mode of adjustment, a sample of purified air is taken from conduit 4 at point 17 and is sent via conduit 18 to an analyzer 19, for example incorporating UV absorber, metering the residual ozone. An output signal from the analyzer is sent to a regulation device 20 which, by a line 21, sends an order of adjustment to a control valve 14 interposed in conduit 11. In this way, the rate of flow of ozone introduced may be adjusted as a function of a reference value, for example 0.1 ppm, of the quantity of ozone metered in the effluent air leaving the washing apparatus through conduit 4.

It will be noted that no heating means is provided, the ozone being introduced at ambient temperature and the aqueous solution itself being at ambient temperature. With the installation shown, Applicant has carried out tests and has established the rate or purification for different identified pollutants and for four types of washing, namely:
(A) Washing with tap water (water lost)
(B) Washing with 5% hydrogen peroxide
(C) Washing with tap water (water lost)+ozone, as is known per se
(D) Washing according to the process of the invention.

The yields expressed in percentage of purification rate are shown in the following Table.

| Pollutant | Type of washing | | | |
|---|---|---|---|---|
| | A | B | C | D |
| Hydrogen sulfide | 0.5% | 54% | ~100% | ~100% |
| Methyl mercaptan | 2 | 7.2 | 60 | 68 |
| Acrolein | 47.5 | 82 | 47.5 | 82 |
| Trimethylamine | 97 | 97 | 97 | 97 |
| Ammonia | ~100 | ~100 | ~100 | ~100 |
| Methylethylketone | 75.2 | 79 | 75.2 | 79 |
| Valeraldehyde | 6.6 | 84 | 6.6 | 84 |
| Butyraldehyde | 43 | 94 | 43 | 94 |

The most surprising point is not so much the rate of yield but that it was obtained without addition of hydrogen peroxide other than the initial 5%. What is also very surprizing is the very small, virtually stoichiometric quantity of consumption of ozone allowed by the process of the invention.

I claim:

1. A process for deodorizing polluted air containing foul-smelling, noxious gaseous residues of organic origin comprising aldehydes or ketones and removing the objectionable smell therefrom said process comprising:
   (1) providing a continuous, closed-circuit flow of an aqueous hydrogen peroxide solution and circulating same within a closed circuit;
   (2) passing the polluted, foul-smelling air to be deodorized through the circulating aqueous hydrogen peroxide solution;
   (3) bubbling ozone into the circulating aqueous hydrogen peroxide solution and thereby supplementing and maintaining the hydrogen peroxide content of said solution within predetermined values in an amount effective to deodorize the air being treated; and
   (4) continuing to circulate and recirculate the ozone-supplemental aqueous hydrogen peroxide solution while contacting the air to be treated with the solution.

2. The process of claim 1 in which the ozone is introduced at ambient temperature and the aqueous solution is itself at ambient temperature.

3. The process of claim 1 in which the ozone is introduced by bubbling through the aqueous solution contained in a buffer tank wherein said buffer tank is part of said closed circuit.

4. The process of claim 1 in which, after introduction of the ozone in the aqueous washing solution, any non-absorbed ozone gas is recovered and introduced into the polluted air before the latter is contacted by said aqueous solution.

5. The process of claim 1 in which initially the amount of hydrogen peroxide in the aqueous solution is between 0.5 and 10% by weight.

6. The process of claim 5 in which the amount of hydrogen peroxide is about 5% by weight.

7. The process of claim 1 which, in addition to a ketone or an aldehyde, the foul-smelling, noxious gas to be treated also contains at least one member selected from the group consisting of reduced compounds, hydrogen sulfide, mercaptans and ammonia.

8. The process of claim 7 wherein the ozone is introduced in equimolecular quantity with respect to the quantity of reduced sulfurated compounds contained in the air to be deodorized.

9. The process of claim 8 including (1) metering the quantity of ozone contained in the effluent air leaving the washing apparatus, and (2) adjusting the rate of flow of ozone so introduced as a function of a predetermined value of the quantity of ozone metered in the effluent air leaving the washing apparatus.

* * * * *